US011760785B2

(12) United States Patent
Gu et al.

(10) Patent No.: US 11,760,785 B2
(45) Date of Patent: Sep. 19, 2023

(54) GLUCOSE TRANSPORTER INHIBITOR-MODIFIED INSULIN FOR GLUCOSE-RESPONSIVE INSULIN DELIVERY

(71) Applicant: NORTH CAROLINA STATE UNIVERSITY, Raleigh, NC (US)

(72) Inventors: Zhen Gu, Los Angeles, CA (US); Jinqiang Wang, Raleigh, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 378 days.

(21) Appl. No.: 16/755,183

(22) PCT Filed: Oct. 10, 2018

(86) PCT No.: PCT/US2018/055202
§ 371 (c)(1),
(2) Date: Apr. 10, 2020

(87) PCT Pub. No.: WO2019/075052
PCT Pub. Date: Apr. 18, 2019

(65) Prior Publication Data
US 2020/0239538 A1    Jul. 30, 2020

Related U.S. Application Data

(60) Provisional application No. 62/570,501, filed on Oct. 10, 2017.

(51) Int. Cl.
| | |
|---|---|
| *C07K 14/62* | (2006.01) |
| *A61K 47/54* | (2017.01) |
| *C07K 14/705* | (2006.01) |
| *A61K 9/00* | (2006.01) |
| *A61K 9/70* | (2006.01) |
| *A61K 38/00* | (2006.01) |

(52) U.S. Cl.
CPC ............ *C07K 14/62* (2013.01); *A61K 47/545* (2017.08); *C07K 14/705* (2013.01); *A61K 9/0021* (2013.01); *A61K 9/7023* (2013.01); *A61K 38/00* (2013.01)

(58) Field of Classification Search
CPC ....... C07K 14/62; C07K 14/705; A61K 47/54
See application file for complete search history.

(56) References Cited

U.S. PATENT DOCUMENTS

2016/0030324 A1    2/2016  Lu et al.

FOREIGN PATENT DOCUMENTS

| WO | 2016/172320 A1 | 10/2016 |
| WO | 2017/124102 A1 | 7/2017 |

OTHER PUBLICATIONS

A. D. Association, Clinical Diabetes 2017, 35, 5-26.
A. Matsumoto, R. Yoshida, K. Kataoka, Biomacromolecules 2004, 5, 1038-1045.
A. Sasaki, K. Nagatomo, K. Ono, T. Yamamoto, Y. Otsuka, T. Teshima, K. Yamada, Human cell 2016, 29, 37-45.
A. Solini, C. Rossi, C. M. Mazzanti, A. Proietti, H. Koepsell, E. Ferrannini, Diabetes, Obesity and Metabolism 2017, 19:1289-1294.
C. Higuchi, T. Sanaka, T. Sato, M. Omata, M. Watanabe, S. Mine, N. Inuzuka, H. Nihei, Advances In Peritoneal Dialysis 1997, 13, 253-256.
C. R. Gordijo, K. Koulajian, A. J. Shuhendler, L. D. Bonifacio, H. Y. Huang, S. Chiang, G. A. Ozin, A. Giacca, X. Y. Wu, Advanced Functional Materials 2011, 21, 73-82.
D. H.-C. Chou, M. J. Webber, B. C. Tang, A. B. Lin, L. S. Thapa, D. Deng, J. V. Truong, A. B. Cortinas, R. Langer, D. G. Anderson, Proceedings of the National Academy of Sciences 2015, 112, 2401-2406.
D. Shiino, Y. Murata, A. Kubo, Y. J. Kim, K. Kataoka, Y. Koyama, A. Kikuchi, M. Yokoyama, Y. Sakurai, T. Okano, Journal of controlled release 1995, 37, 269-276.
J. D. Robbins, A. Laurenza, R. W. Kosley Jr, G. J. O'Malley, B. Spahl, K. B. Seamon, Journal of medicinal chemistry 1991, 34, 3204-3212.
J. R. Ehrenkranz, N. G. Lewis, C. R. Kahn, J. Roth, Diabetes Metab Res Rev 2005, 21, 31-38.
J. Yu, Y. Zhang, Y. Ye, R. DiSanto, W. Sun, D. Ranson, F. S. Ligler, J. B. Buse, Z. Gu, Proc Natl Acad Sci U S A 2015, 112, 8260-8265.
K. Kapoor, J. S. Finer-Moore, B. P. Pedersen, L. Caboni, A. Waight, R. C. Hillig, P. Bringmann, I. Heisler, T. Müller, H. Siebeneicher, Proceedings of the National Academy of Sciences 2016, 113, 4711-4716.
K. M. Bratlie, R. L. York, M. A. Invernale, R. Langer, D. G. Anderson, Adv Healthc Mater 2012, 1, 267-284.
K. Podual, F. J. Doyle, N. A. Peppas, Journal of Controlled Release 2000, 67, 9-17.
M. Brownlee, A. Cerami, Diabetes 1983, 32, 499-504.
M. F. Shanahan, S. A. Olson, M. J. Weber, G. E. Lienhard, J. C. Gorga, Biochemical and biophysical research communications 1982, 107, 38-43.
M. L. Macheda, S. Rogers, J. D. Best, Journal of cellular physiology 2005, 202, 654-662.
N. Manel, F. J. Kim, S. Kinet, N. Taylor, M. Sitbon, J.-L. Battini, Cell 2003, 115, 449-459.
N. Peppas, Y. Huang, M. Torres-Lugo, J. Ward, J. Zhang, Annual review of biomedical engineering 2000, 2, 9-29.
N. Yan, Journal of Molecular Biology 2017, 429, 2710-2725.
O. Veiseh, B. C. Tang, K. A. Whitehead, D. G. Anderson, R. Langer, Nat Rev Drug Discov 2015, 14, 45-57.
R. L. Ingermann, J. M. Bissonnette, P. L. Koch, Biochimica et Biophysica Acta (BBA)-Biomembranes 1983, 730, 57-63.

(Continued)

*Primary Examiner* — Gyan Chandra
(74) *Attorney, Agent, or Firm* — Meunier Carlin & Curfman LLC (57) ABSTRACT

Disclosed herein is a glucose-responsive insulin delivery system based on the interaction between the glucose-modified insulin and glucose transporters (GLUTs) on erythrocytes (or red blood cells, RBCs). After being conjugated with a competitive inhibitor of a glucose transporter, insulin can efficiently bind to RBC membranes. The binding is reversible in the setting of hyperglycemia, resulting in fast release of insulin and subsequent drop of blood glucose (BG) level in vivo.

16 Claims, 4 Drawing Sheets

(56) References Cited

OTHER PUBLICATIONS

S. Kohler, A. Salsali, S. Hantel, S. Kaspers, H. J. Woerle, G. Kim, U. C. Broedl, Clinical Therapeutics 2016, 38, 1299-1313.

W. L. Brooks, B. S. Sumerlin, Chemical reviews 2015, 116, 1375-1397.

X. Hu, J. Yu, C. Qian, Y. Lu, A. R. Kahkoska, Z. Xie, X. Jing, J. B. Buse, Z. Gu, ACS Nano 2017, 11, 613-620.

Y. Ito, M. Casolaro, K. Kono, Y. Imanishi, Journal of controlled release 1989, 10, 195-203.

Y. Lu, A. A. Aimetti, R. Langer, Z. Gu, Nature Reviews Materials 2016, 2, 16075.

Y. Ohkubo, H. Kishikawa, E. Araki, T. Miyata, S. Isami, S. Motoyoshi, Y. Kojima, N. Furuyoshi, M. Shichiri, Diabetes research and clinical practice 1995, 28, 103-117.

Z. Gu, A. A. Aimetti, Q. Wang, T. T. Dang, Y. Zhang, O. Veiseh, H. Cheng, R. S. Langer, D. G. Anderson, ACS Nano 2013, 7, 4194-4201.

Z. Gu, T. T. Dang, M. Ma, B. C. Tang, H. Cheng, S. Jiang, Y. Dong, Y. Zhang, D. G. Anderson, ACS Nano 2013, 7, 6758-6766.

International Preliminary Report on Patentability issued for Application No. PCT/US2018/055202, dated Apr. 23, 2020.

Lu et al. "D-Glucose, forskolin and cytochalasin B affinities for the glucose transporter Glut1: 1-3, 9-12 Study of pH and reconstitution effects by biomembrane affinity chromatography," J Chromatogr. A, Jul. 25, 1997 (Jul. 25, 1997), vol. 776.

Lavis et al. "Evidence that forskolin binds to the glucose transporter of human erythrocytes," J 1-3, 9-12 Biol Chem, Oct. 25, 1987 (Oct. 25, 1987), vol. 262.

Sergeant et al. "Inhibition of 3-O-methylglucose transport in human erythrocytes by 1-3, 9-12 forskolin," J Biol Chem, Nov. 25, 1985 (Nov. 25, 1985), vol. 2600.

Wang et al. "Red Blood Cells for Glucose-Responsive Insulin Delivery," Adv Mater, Mar. 1-3, 7, 9-12, 2017 (Mar. 7, 2017), vol. 29.

International Search Report and Written Opinion, issued in corresponding application No. PCT/US2018/055202, dated Dec. 27, 2018, 10 pages.

GLUCOSE TRANSPORTER INHIBITOR-MODIFIED INSULIN FOR GLUCOSE-RESPONSIVE INSULIN DELIVERY

This is a national phase application filed under 35 U.S.C. § 371 of PCT International Application No. PCT/US2018/055202, filed on Oct. 10, 2018, entitled "GLUCOSE TRANSPORTER INHIBITOR-MODIFIED INSULIN FOR GLUCOSE-RESPONSIVE INSULIN DELIVERY," which claims the benefit of, U.S. Provisional Application No. 62/570,501, filed Oct. 10, 2017, applications which are incorporated herein by reference in their entireties.

BACKGROUND

Diabetes currently affects 415 million people worldwide and this number is expected to increase to 642 million by 2040. Insulin is essential for survival in type 1 diabetes and often required for treatment of type 2 diabetes in order to control glycemia and prevent complications. However, traditional exogenous insulin administration cannot match the exquisite regulation of blood glucose achieved by β-cells within the pancreatic islets of Langerhans, where endogenous insulin secretion is linked through metabolism to glucose transport. Poor glucose control results in a high risk for diabetes complications, such as limb amputation, blindness and kidney failure. In addition, hypoglycemia can lead to behavioral and cognitive disturbance, seizure, coma, brain damage, or death. "Smart" glucose-responsive insulin delivery devices or formulations, which can mimic the function of β-cells to regulate insulin "secretion," are therefore highly desirable with an aim to improve blood glucose control and quality of life for people with diabetes.

Such "smart" therapies generally integrate a glucose-sensing or conversion module and a sensing/conversion-activated insulin releasing module. For example, the wearable closed-loop electronic/mechanical pumps combine a continuous glucose-monitoring electrochemical sensor and an external insulin infusion pump. These systems have historically been limited by lag in blood glucose equilibration with the interstium, insulin absorption into the circulation and biofouling. Synthetic materials-based glucose-responsive formulations have also been widely explored since the 1970's. Three classical strategies are often utilized, typically including different glucose-sensing moieties: glucose oxidase, glucose binding proteins (GPB) (e.g., ConA) (14) and phenylboronic acid (PBA) for achieving glucose triggers. A variety of formulations, such as bulk hydrogels, microgels, emulsion-based nanoparticles and self-assembled vesicles have been developed to respond toward a hyperglycemic state to swell, shrink, degrade, or dissociate in order to promote the release of insulin. In spite of these promising strategies, it remains challenging to demonstrate a system that responds rapidly to elevated blood glucose levels (BGLs), closely mirroring the kinetics of a healthy pancreas. In addition, immunological responses, stability in the physiological environment and long-term toxicity of those synthetic systems require further investigation.

SUMMARY

Disclosed herein are glucose-responsive insulin delivery compositions that can be used to control glucose levels in a subject. In particular, a composition is disclosed that comprises a glucose-transporter binding structure that comprises an insulin moiety conjugated to at least one competitive inhibitor of glucose transporter. In these embodiments, the glucose-transporter binding structure is configured to reversibly bind a glucose transporter and for insulin to reversibly bind to the competitive inhibitor of glucose transporter such that the glucose-modified insulin is displaced by endogenous glucose in high glucose conditions. This results in the bioavailability of the glucose-modified insulin molecule where it can promote glucose metabolism. Since the rate of release is dependent on glucose concentration, glucose levels can be tightly regulated.

The insulin moiety can any bioactive form of insulin, such as human insulin or an insulin homologue. The insulin is preferably a recombinant protein. The insulin can be rapid-acting (e.g. lispro, aspart, glulisine), short-acting (regular insulin, velosulin, novolin), intermediate-acting (NPH), or long-acting (insulin glargine, insulin detemir, insulin degludec). In some embodiments, the disclosed composition comprises a mixture of glucose-modified insulin molecules having different forms of insulin moieties.

It is understood and herein contemplated that the competitive inhibitor or the glucose transporter can be any competitive inhibitor that binds to a glucose transporter with greater affinity and/or avidity than D-glucose and capable of reversibly binding glucose transporter in vivo. For example, the competitive inhibitor of a glucose transporter can be forskolin or In2.

In some cases, the user mixes the composition comprising the insulin molecule with a competitive inhibitor of a glucose transporter prior to administration to a subject under conditions suitable for the glucose-modified insulin molecule to reversibly bind the glucose binding structure. In other embodiments, the composition comprises insulin molecule already bound to the competitive inhibitor of a glucose transporter.

The competitive inhibitor of a glucose transporter can be any biocompatible molecule or substrate capable of reversibly binding glucose transporter in vivo. It is understood and herein contemplated that a glucose transporter can comprise any glucose transporter (GLUT) protein family member (including, but not limited to GLUT1, GLUT2, GLUT3, GLUT4, GLUT5, GLUT6, GLUT7, GLUT8, GLUT9, GLUT10, GLUT11, GLUT12, GLUT13, and GLUT14), which are membrane proteins that facilitates the transport of glucose over a plasma membrane. GLUT1 is a glucose transporter that is expressed at highest levels in red blood cells (erythrocytes). Therefore, in particular embodiments, the glucose-binding structure is a red blood cell (erythrocyte), such as a human red blood cell. However, in other embodiments, the glucose-binding structure comprises only the plasma membrane of an erythrocyte, or other cell that comprises a GLUT protein. For example, the plasma membrane can be attached to a biocompatible nanoparticle. Suitable nanoparticles can in some embodiments have a mean diameter of about 50 to about 150 nanometers, including about 50, 60, 70, 80, 90, 100, 110, 120, 130, 140, and 150 nanometers. In some embodiments, the nanoparticle comprises Poly(Lactide-co-Glycolide) (PLGA) copolymer. In some embodiments, the nanoparticle is formed from dextran. In some embodiments, the nanoparticle is formed from hyaluronic acid. In some embodiments, the nanoparticle is a liposome.

The glucose transporter binding structure is configured for the competitive inhibitor of the glucose transporter to be displaced from the glucose-transporter and insulin to be displaced from the competitive inhibitor of the glucose transporter in high glucose conditions. In some embodiments, the glucose transporter binding structure is configured for the competitive inhibitor of the glucose transporter to be displaced from the glucose transporter and to release insulin when glucose levels reach or exceed about 200 mg/dL. While it is understood that the competitive inhibitor of the glucose transporter can still be displaced from the glucose transpoter at low glucose levels, it will do so at a much lower rate. Therefore, in some embodiments, the competitive inhibitor of the glucose transporter preferentially binds the glucose transporter in a physiological, low glucose environment, e.g. glucose concentrations from 0 to 200 mg/dL. In preferred embodiments, the competitive inhibitor of the glucose transporter is configured to stably bind the glucose transporter in these low glucose conditions for at least 10, 20, 30, 40, or 50 days. In some embodiments, these kinetics can be tuned through the linker property between hormone and the glucose-derivative.

Also disclosed is a method of controlling glucose levels in a subject, the method comprising; administering a therapeutically effective amount of a composition to a subject having diabetes, the composition comprising a glucose transporter binding structure comprising an insulin moiety conjugated to at least one competitive inhibitor of glucose transporter, wherein the glucose transporter binding structure is configured to reversibly bind a glucose transporter, and wherein the glucose-binding structure releases a portion of the glucose-modified insulin in high glucose conditions.

The disclosed composition can be administered in any manner suitable for exposure to glucose in the circulation. In some embodiments, the composition is delivered by a transdermal patch. For example, the composition can be delivered by a microneedle-array patch. In other aspects the composition can be administered orally.

The details of one or more embodiments of the invention are set forth in the accompanying drawings and the description below. Other features, objects, and advantages of the invention will be apparent from the description and drawings, and from the claims.

DETAILED DESCRIPTION

Definitions

Terms used throughout this application are to be construed with ordinary and typical meaning to those of ordinary skill in the art. However, Applicant desires that the following terms be given the particular definition as defined below.

As used in the specification and claims, the singular form "a," "an," and "the" include plural references unless the context clearly dictates otherwise. For example, the term "a cell" includes a plurality of cells, including mixtures thereof.

The terms "about" and "approximately" are defined as being "close to" as understood by one of ordinary skill in the art. In one non-limiting embodiment the terms are defined to be within 10%. In another non-limiting embodiment, the terms are defined to be within 5%. In still another non-limiting embodiment, the terms are defined to be within 1%.

"Activities" of a protein, including those relating to "bioactivity," include, for example, transcription, translation, intracellular translocation, secretion, phosphorylation by kinases, cleavage by proteases, and/or homophilic and heterophilic binding to other proteins.

The term "administering" refers to an administration that is oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation or via an implanted reservoir. Administering can be performed using transdermal microneedle-array patches. The term "parenteral" includes subcutaneous, intravenous, intramuscular, intra-articular, intra-synovial, intrasternal, intrathecal, intrahepatic, intralesional, and intracranial injections or infusion techniques.

"Biocompatible" generally refers to a material and any metabolites or degradation products thereof that are generally non-toxic to the recipient and do not cause any significant adverse effects to the subject.

A "composition" is intended to include a combination of active agent and another compound or composition, inert (for example, a detectable agent or label) or active, such as an adjuvant.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

A "control" is an alternative subject or sample used in an experiment for comparison purpose. A control can be "positive" or "negative."

As used herein, "conjugated" refers to a non-reversible binding interaction.

As used herein, "displace" refers to interrupting a molecular or chemical interaction between, for example, a protein domain and a peptide, a protein domain and a chemical, a protein domain and a nucleic acid sequence by a chemical, peptide, or nucleic acid having affinity for that specific protein domain than the peptide, chemical, or nucleic acid being displaced.

An "effective amount" is an amount sufficient to effect beneficial or desired results. An effective amount can be administered in one or more administrations, applications or dosages.

As used herein, the term "high glucose conditions" refers to an environment having a glucose concentration greater than or equal to 200 mg/dL. For example, "high blood glucose levels" refer to glucose levels in the blood stream greater than or equal to 200 mg/dL. In some embodiments, high glucose conditions are 200-400 mg/dL. In other embodiments, high glucose conditions are 300-400 mg/dL.

A "linker" as used herein refers to a molecule that joins adjacent molecules. Generally a linker has no specific biological activity other than to join the adjacent molecules or to preserve some minimum distance or other spatial relationship between them. In some cases, the linker can be selected to influence or stabilize some property of the adjacent molecules, such as the folding, net charge, or hydrophobicity of the molecule.

As used herein, the term "low glucose conditions" refers to an environment having a glucose concentration from 0 to 200 mg/dL. For example, "low blood glucose levels" refer to glucose levels in the blood stream less than 200 mg/dL.

The terms "peptide," "protein," and "polypeptide" are used interchangeably to refer to a natural or synthetic molecule comprising two or more amino acids linked by the carboxyl group of one amino acid to the alpha amino group of another.

The term "carrier" or "pharmaceutically acceptable carrier" means a carrier or excipient that is useful in preparing a pharmaceutical or therapeutic composition that is generally safe and non-toxic, and includes a carrier that is acceptable for veterinary and/or human pharmaceutical or therapeutic use. As used herein, the terms "carrier" or "pharmaceutically acceptable carrier" encompasses can include phosphate buffered saline solution, water, emulsions (such as an oil/water or water/oil emulsion) and/or various types of wetting agents. As used herein, the term "carrier" encompasses any excipient, diluent, filler, salt, buffer, stabilizer, solubilizer, lipid, stabilizer, or other material well known in the art for use in pharmaceutical formulations and as described further below.

As used herein, the term "polymer" refers to a relatively high molecular weight organic compound, natural or synthetic, whose structure can be represented by a repeated small unit, the monomer (e.g., polyethylene, rubber, cellulose). Synthetic polymers are typically formed by addition or condensation polymerization of monomers. As used herein, the term "copolymer" refers to a polymer formed from two or more different repeating units (monomer residues). By way of example and without limitation, a copolymer can be an alternating copolymer, a random copolymer, a block copolymer, or a graft copolymer. It is also contemplated that, in certain aspects, various block segments of a block copolymer can themselves comprise copolymers.

A "primer" is a short polynucleotide, generally with a free 3'-OH group that binds to a target or "template" potentially present in a sample of interest by hybridizing with the target, and thereafter promoting polymerization of a polynucleotide complementary to the target. A "polymerase chain reaction" ("PCR") is a reaction in which replicate copies are made of a target polynucleotide using a "pair of primers" or a "set of primers" consisting of an "upstream" and a "downstream" primer, and a catalyst of polymerization, such as a DNA polymerase, and typically a thermally-stable polymerase enzyme. Methods for PCR are well known in the art, and taught, for example in "PCR: A PRACTICAL APPROACH" (M. MacPherson et al., IRL Press at Oxford University Press (1991)). All processes of producing replicate copies of a polynucleotide, such as PCR or gene cloning, are collectively referred to herein as "replication." A primer can also be used as a probe in hybridization reactions, such as Southern or Northern blot analyses. Sambrook et al., supra.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed.

The terms "therapeutically effective amount" or "therapeutically effective dose" refer to the amount of a composition, such as glucose-modified insulin bound to a glucose-binding structure, that will elicit the biological or medical response of a tissue, system, animal, or human that is being sought by the researcher, veterinarian, medical doctor or other clinician over a generalized period of time. In some embodiments, a desired response is the control of type I diabetes. In some embodiments, a desired response is the control of type II diabetes. In some instances, a desired biological or medical response is achieved following administration of multiple dosages of the composition to the subject over a period of days, weeks, or years.

The term "subject" is defined herein to include animals such as mammals, including, but not limited to, primates (e.g., humans), cows, sheep, goats, horses, dogs, cats, rabbits, rats, mice and the like. In some embodiments, the subject is a human.

"Transformation" of a cellular organism with DNA means introducing DNA into an organism so that at least a portion of the DNA is replicable, either as an extrachromosomal element or by chromosomal integration. "Transfection" of a cellular organism with DNA refers to the taking up of DNA, e.g., an expression vector, by the cell or organism whether or not any coding sequences are in fact expressed. The terms "transfected host cell" and "transformed" refer to a cell in which DNA was introduced. The cell is termed "host cell" and it may be either prokaryotic or eukaryotic. Typical prokaryotic host cells include various strains of E. coli. Typical eukaryotic host cells are mammalian, such as Chinese hamster ovary or cells of human origin. The introduced DNA sequence may be from the same species as the host cell of a different species from the host cell, or it may be a hybrid DNA sequence, containing some foreign and some homologous DNA.

The terms "treat," "treating," "treatment," and grammatical variations thereof as used herein, include partially or completely delaying, alleviating, mitigating or reducing the intensity of one or more attendant symptoms of a disorder or condition and/or alleviating, mitigating or impeding one or more causes of a disorder or condition. Treatments according to the invention may be applied preventively, prophylactically, palliatively or remedially. Prophylactic treatments are administered to a subject prior to onset (e.g., before obvious signs of cancer), during early onset (e.g., upon initial signs and symptoms of cancer), or after an established development of cancer. Prophylactic administration can occur for several days to years prior to the manifestation of symptoms of an infection.

In some instances, the terms "treat", "treating," "treatment" and grammatical variations thereof, include controlling blood sugar levels and reducing the severity of diabetes symptoms as compared with prior to treatment of the subject or as compared with the incidence of such symptom in a general or study population.

The term "specifically binds," as used herein, when referring to a polypeptide (including antibodies) or receptor, refers to a binding reaction which is determinative of the presence of the protein or polypeptide or receptor in a heterogeneous population of proteins and other biologics. Thus, under designated conditions (e.g. immunoassay conditions in the case of an antibody), a specified ligand or antibody "specifically binds" to its particular "target" (e.g. an antibody specifically binds to an endothelial antigen) when it does not bind in a significant amount to other proteins present in the sample or to other proteins to which the ligand or antibody may come in contact in an organism. Generally, a first molecule that "specifically binds" a second molecule has an affinity constant (Ka) greater than about $10^5$ $M^{-1}$ (e.g., $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, and $10^{12}$ $M^{-1}$ or more) with that second molecule.

Composition and Methods

Disclosed herein is a composition and method for treating diabetes. The composition includes a glucose transporter binding structure that includes an insulin moiety conjugated to at least one competitive inhibitor of a glucose transporter.

The insulin moiety can any bioactive form of insulin, such as human insulin or an insulin homologue. The insulin is preferably a recombinant protein. The insulin can be rapid-acting (e.g. lispro, aspart, glulisine), short-acting (regular insulin, velosulin, novolin), intermediate-acting (NPH), or long-acting (insulin glargine, insulin detemir, insulin degludec). In some embodiments, the disclosed composition comprises a mixture of glucose-modified insulin molecules having different forms of insulin moieties.

It is understood and herein contemplated that the competitive inhibitor of the glucose transporter can be any competitive inhibitor that binds to a glucose transporter with greater affinity and/or avidity than D-glucose and capable of reversibly binding glucose transporter in vivo. For example, the competitive inhibitor of a glucose transporter can be cytochalasin B, phloretin, forskolin or In2. The competitive inhibitor of a glucose transporter can be any biocompatible molecule or substrate capable of reversibly binding glucose transporter in vivo. It is understood and herein contemplated that a glucose transporter can comprise any glucose transporter (GLUT) protein family member (including, but not limited to GLUT1, GLUT2, GLUT3, GLUT4, GLUT5, GLUT6, GLUT7, GLUT8, GLUT9, GLUT10, GLUT11, GLUT12, GLUT13, and GLUT14), which are membrane proteins that facilitates the transport of glucose over a plasma membrane.

In some cases, the user mixes the composition comprising the insulin molecule with a competitive inhibitor of a glucose transporter prior to administration to a subject under conditions suitable for the glucose-modified insulin molecule to reversibly bind the glucose binding structure. In other embodiments, the composition comprises insulin molecule already bound to the competitive inhibitor of a glucose transporter.

The glucose-transporter binding structure comprising one or more competitive inhibitors of a glucose transporter and insulin include, but are not limited to, structures such as a cell, a cell membrane, a nanoparticle and a microparticle. Accordingly, in some implementations, the glucose-binding structure is a cell. The cell may be any cell type, human, mammalian. In some examples, the cells used as glucose-binding structures are human red blood cells. Advantageously, autologously derived cells may be drawn from a subject, exposed to the glucose-modified insulin in low-glucose (binding) conditions, and then delivered back to the same subject. However, the cells need not be autologously derived for the composition to serve the function of releasing bound competitive inhibitor of a glucose transporter-insulin under high glucose conditions.

GLUT1 is a glucose transporter that is expressed at highest levels in red blood cells (erythrocytes). Therefore, in particular embodiments, the glucose-binding structure is a red blood cell (erythrocyte), such as a human red blood cell. However, in other embodiments, the glucose-binding structure comprises only the plasma membrane of an erythrocyte, or other cell that comprises a GLUT protein. For example, the plasma membrane can be attached to a biocompatible nanoparticle. In other implementations, the glucose transporter binding structure is a red blood cell membrane attached to a nanoparticle or a microparticle. The nanoparticle can have any appropriate measurement. For example, nanoparticle sizes can range from 5 to 500 nanometers in diameter. In some implementations, nanoparticle sizes measure between 50-150 nanometers in diameter. Suitable nanoparticles can in some embodiments have a mean diameter of about 50 to about 150 nanometers, including about 50, 60, 70, 80, 90, 100, 110, 120, 130, 140, and 150 nanometers. The nanoparticle can also be of any appropriate material or substance, and in some implementations, is a poly lactic-co-glycolic acid (PLGA) nanoparticle. For example, PLGA nanoparticles (NPs) can be coated with RBC membranes (RM-PLGA) using similar methods as those described below. As with intact mRBCs, The competitive inhibitor of a glucose transporter-Insulin can likewise bind to RM-PLGA NPs specifically and release insulin from these nanoparticles, and said release can be self-regulated in a BG-mediated manner Other nanomaterials or nanoparticles may be used as an alternative or in addition to PLGA. Other possible nanomaterials or nanoparticles can include polymeric materials (for example, dextran or hyaluronic acid), liposomes, and/or inorganic nanoparticles.

In some implementations, the glucose transporter binding structure can comprise two or more competitive inhibitors of a glucose transporter. In some implementations, each glucose transporter competitive inhibitor is conjugated to the insulin moiety by a distinct linker molecule. The linker molecule can be any natural or synthetic molecule that serves to attach the glucose moiety to the insulin moiety. In some examples, the linker molecule includes a maleimide group, or a maleimide-thiol adduct. In a particular example, a maleimide group is added to a glucose molecule, and a thiol group is added to an insulin molecule. The maleimide-glucose and thiolated insulin are then reacted to form the glucose-modified insulin molecule, wherein the maleimide-thiol adduct acts as a linker molecule. Alternatively, or in addition, the linker molecule can include a spacer. The spacer may be a polymer chain, such as a poly(ethylene glycol) (PEG) chain or a chain of any other suitable polymer.

The invention includes a composition for glucose-responsive insulin delivery based on the reversible interaction between a competitive inhibitor of glucose transporter and a glucose transporter. Such binding is reversible, and insulin can be released from RBCs under high glucose conditions. Accordingly, disclosed herein are glucose responsive insulin systems wherein the competitive inhibitor of a glucose transporter is configured to reversibly bind a glucose transporter, releasing the competitive inhibitor of a glucose transporter in high glucose conditions. A potential mechanism for this release is the displacement of the competitive inhibitor of a glucose transporter-Insulin (CIG-Ins) due to competitive interaction of free glucose with GLUT. Human RBCs have a life span of 100-120 days as natural carriers for oxygen in the blood vessels. Therefore, these inherently biocompatible natural carriers could prolong the circulation of medicine in blood. In the following examples, intravenous (i.v.) injection of mouse RBCs (mRBCs) coupled with CIG-Ins is shown to prolong the therapeutic effect of insulin to maintain blood glucose levels (BGLs) within the normal range compared with free insulin in chemically induced type I mice. In vivo glucose-responsive behavior was observed through a glucose tolerance test. Alternate strategies of administration include 1) i.v. injectable polymeric nanoparticles (approximately 100 nm in diameter) coated with RBC membrane and loaded with glucose-modified insulin and 2) a microneedle (MN) patch platform loaded with the complex of exogenously expressed GLUTs and glucose transporter binding structures.

As noted above the competitive inhibitor of a glucose transporter can be configured to reversibly bind a glucose transporter binding structure. Similarly, the insulin moiety can be configured to reversibly bind the competitive inhibitor of a glucose transporter. The reversible binding can be achieved by non-covalent binding between the glucose and one or more glucose binding moieties. In some implementations, the glucose transporter proteins are bound to the competitive inhibitor of a glucose transporter through non-covalent binding such as a receptor-ligand binding interaction. Non-limiting examples of glucose transporters are all members of the GLUT or SLC2A families, including GLUT1, GLUT2, GLUT3, GLUT4, GLUT5, GLUT6, GLUT7, GLUT8, GLUT9, GLUT10, GLUT11, GLUT12, GLUT13, GLUT14, and SLC2A13.

The glucose transporter binding structure is configured for the competitive inhibitor of the glucose transporter to be displaced from the glucose-transporter and insulin to be displaced from the competitive inhibitor of the glucose transporter in high glucose conditions. In some embodiments, the glucose transporter binding structure is configured for the competitive inhibitor of the glucose transporter to be displaced from the glucose transporter and to release insulin when glucose levels reach or exceed about 200 mg/dL. While it is understood that the competitive inhibitor of the glucose transporter can still be displaced from the glucose transporter at low glucose levels, it will do so at a much lower rate. Therefore, in some embodiments, the competitive inhibitor of the glucose transporter preferentially binds the glucose transporter in a physiological, low glucose environment, e.g. glucose concentrations from 0 to 200 mg/dL. In preferred embodiments, the competitive inhibitor of the glucose transporter is configured to stably bind the glucose transporter in these low glucose conditions for at least 10, 20, 30, 40, or 50 days. In some embodiments, these kinetics can be tuned through the linker property between hormone and the glucose-derivative.

The glucose transporter binding structure is configured to release the competitive inhibitor of the glucose transporter in high glucose conditions. This facilitates the release of a portion of the competitive inhibitor of the glucose transporter-insulin when, for example, blood glucose levels rise above a certain threshold. For example, under high glucose conditions, anywhere from 10%-95% of the glucose-modified insulin molecule may be released from the glucose-binding structure, including 10%, 15%, 20%, 25%, 30%, 35%, 40%, 45%, 50%, 55%, 60%, 65%, 70%, 75%, 80%, 85%, 90%, or 95% of the glucose-modified insulin. As used herein, high glucose conditions are considered to be greater than or equal to 200 mg/dL. In some embodiments, high glucose conditions are 200-400 mg/dL. In other embodiments, high glucose conditions are 300-400 mg/dL. Low glucose conditions are considered to be less than 200 mg/dL. While it is understood that the competitive inhibitor of the glucose transporter can still be displaced from the glucose transpoter at low glucose levels, it will do so at a much lower rate. Therefore, in some embodiments, the competitive inhibitor of the glucose transporter preferentially binds the glucose transporter in a physiological, low glucose environment, e.g. glucose concentrations from 0 to 200 mg/dL. In preferred embodiments, the competitive inhibitor of the glucose transporter is configured to stably bind the glucose transporter in these low glucose conditions for at least 10, 20, 30, 40, or 50 days. In some embodiments, these kinetics can be tuned through the linker property between hormone and the glucose-derivative.

In some implementations, under low glucose conditions, the glucose transporter binding structure is configured to bind the glucose transporter for at least 50 days. In some implementations, the glucose transporter binding structure may bind the glucose transporter for even greater time periods if the glucose conditions remain low. For example, red blood cells have a lifespan of 100-120 days. Competitive inhibitor of the glucose transporter-insulin carried by red blood cells may remain bound for the duration of the lifespan of the cell carrier in low glucose conditions.

Also disclosed herein are methods of using the competitive inhibitor of the glucose transporter-insulin compositions to treat diabetes. The method of treating diabetes includes first administering a composition such as any of those described above, that is, the methods of treating diabetes include providing a composition including the glucose transporter binding structure, wherein the competitive inhibitor of a glucose transporter is bound to insulin. In some implementations, a therapeutically effective amount of glucose-modified insulin molecule bound to a glucose-binding structure is administered to a subject having or suspected of having diabetes. In some implementations, the therapeutically effective amount of a glucose transporter binding structure comprising an insulin moiety conjugated to at least one competitive inhibitor of glucose transporter can be administered via a transdermal patch, such as a microneedle-array patch. In other aspects, the composition can be administered orally It is challenging to demonstrate a combination of fast response, long-term persistence and biocompatibility in glucose-responsive insulin delivery formulations. The glucose-modified insulin strategies described herein present effective approaches. In some examples, these strategies can be extended to personalized cell therapy, and/or integrated with a variety of therapeutics for treating different diseases with merits of both long-term sustained release and physiological signal-mediated controlled release.

EXAMPLES

An ideal insulin formulation should be able to release insulin according to BGLs and tightly regulate it while avoiding the lethal hypoglycemia. Therefore, glucose-responsive insulin formulations mimicking the function of β-cells is desirable for the treatment of diabetes. Recently, various glucose responsive delivery systems based on glucose oxidase (GOx), phenylboronic acid (PBA), and glucose-binding proteins have been vastly investigated and studied. However, these methods encountered several challenges, including poor biocompatibility, low insulin loading efficiency and content, delayed response rate and intricate manipulation processes.

GLUT on membranes facilitates glucose transporting from the extracellular matrix into cells. Therefore, GLUT has been investigated as the target for treatment of type 2 diabetes and cancer. Glucose transporter is distributed almost on all living cells to maintain the energy supply. Including D-glucose, other small molecules, like cytochalasin B, forskolin or phloretin are found to be the substrate of GLUT and possess significantly higher affinity than D-glucose, and have been vastly used in the study of GLUT and cell metabolism. Most importantly and interestingly, the binding of several inhibitors on GLUT was found to be displaceable by D-glucose in a competitive manner.

Figure 1:
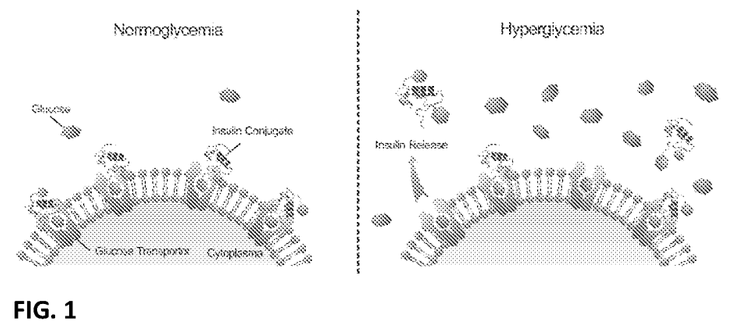
FIG. 1 shows a schematic Schematic of the glucose-responsive insulin delivery system based on GLUT on living cells.

Herein, a new strategy utilizing the in situ living cells as the carrier for insulin was developed. As illustrated in FIG. 1, insulin was first conjugated to GLUT inhibitors (forskolin and In2) via a covalent bond, which can endow the insulin ability to bind to GLUT in vivo and in situ. In addition, the introduction of water-insoluble inhibitors onto insulin can greatly reduce its water solubility at pH 7.4. After subcutaneously injected, insulin conjugate formed a depot beneath the skin, which can slowly release insulin conjugate into the blood. Then, insulin conjugate reaches the GLUT on living cells, including adipose cells, muscle cells and blood cells, during blood circulation and consequently establishing an insulin pool. Of note, the GLUT pool on living cells can also buffer the high level of insulin in blood in the initial period post-injection and works as the reservoir of insulin to smooth the level of blood insulin. The adsorption of insulin-conjugate to cell membranes is in a dynamic balance with insulin conjugate in interstitial fluid and blood under a normoglycemic state. The insulin conjugate binding on living cell membranes can be released in a glucose-triggered manner under a hyperglycemic state because of the competitive binding from elevated glucose level.

Figure 2:
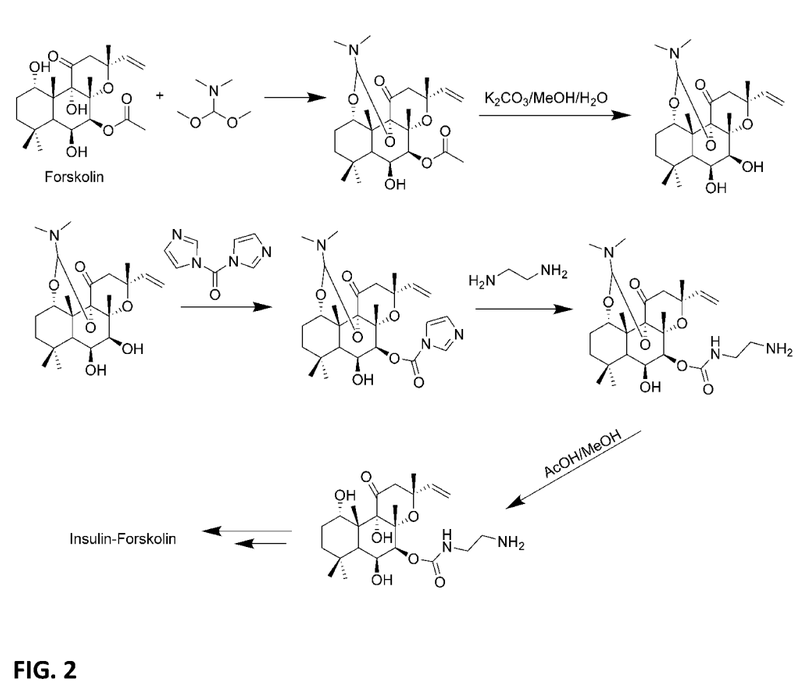
FIG. 2 shows a synthesis route for forskolin-$NH_2$.
Figure 3:
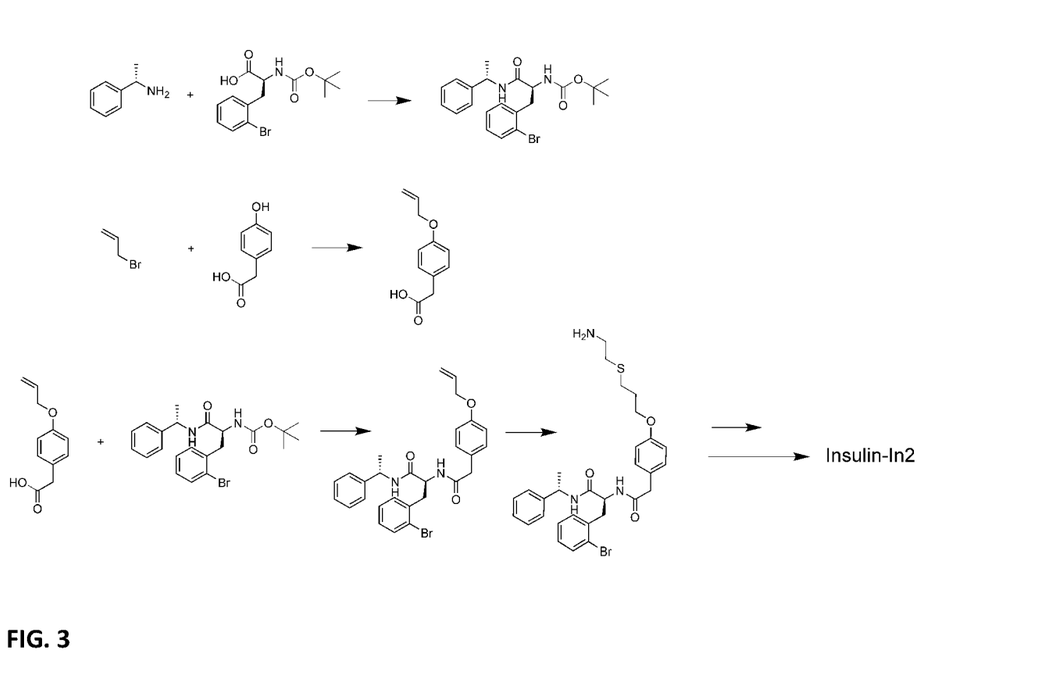
FIG. 3 shows a synthesis route for In2-$NH_2$.
Figure 4:
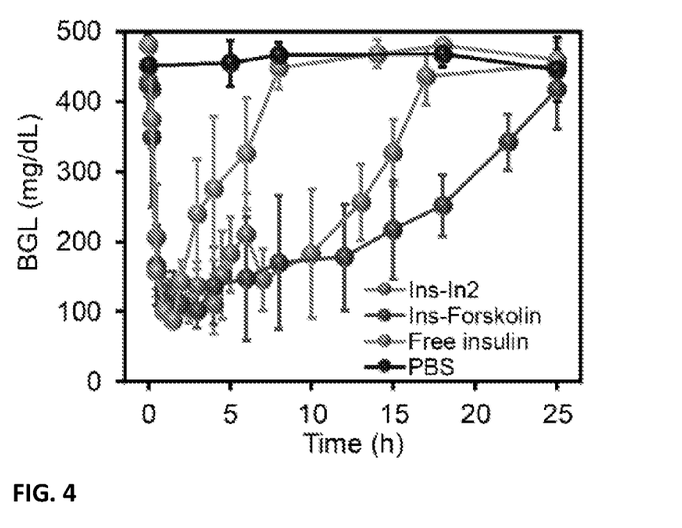
FIG. 4 shows blood glucose levels of type 1 diabetic mice treated with free insulin, insulin-forskolin or insulin-In2. PBS was used as a control. The dose was set to 300 IU/kg for insulin conjugate and 150 IU/kg for free insulin to avoid severe hypoglycemia. Error bars represent the S.D. of three independent experiments (n=3).
Figure 5:
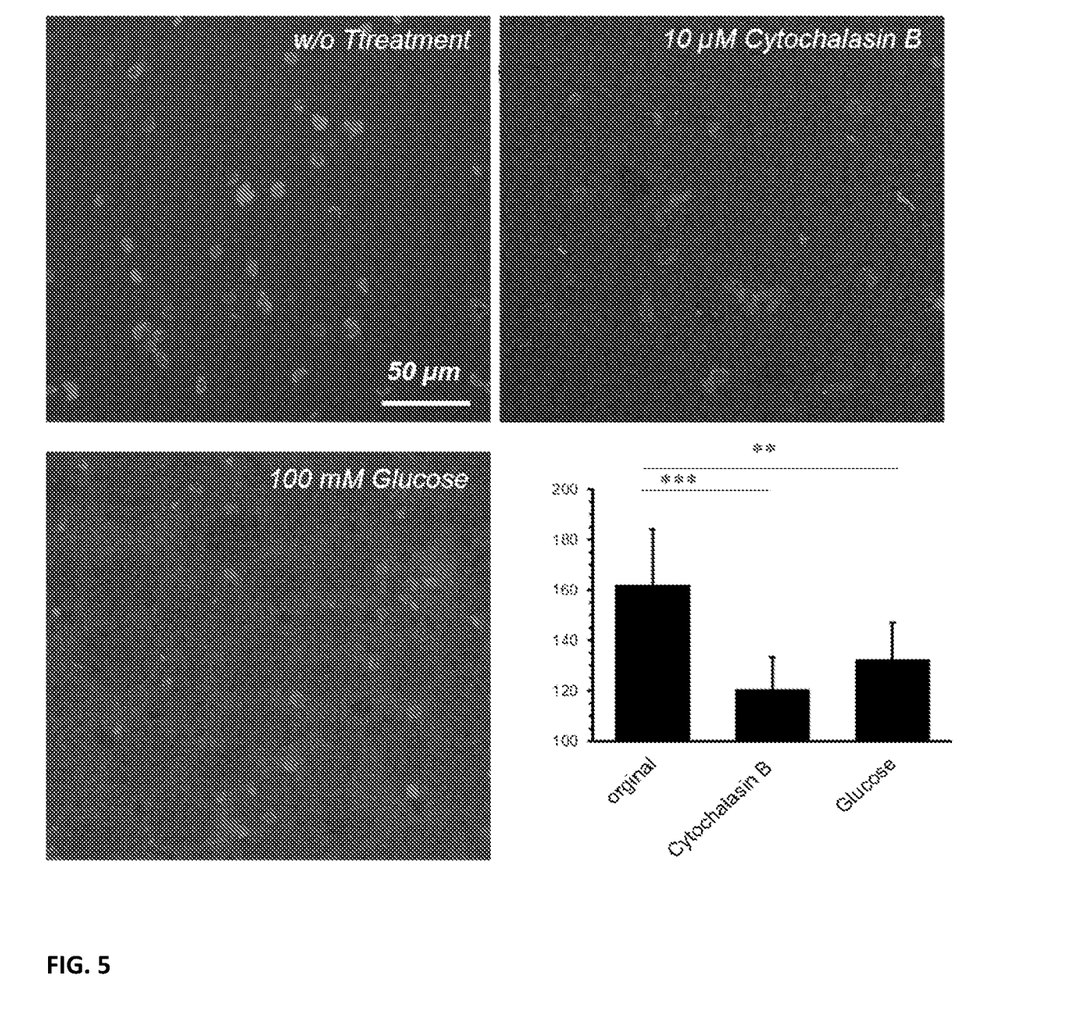
FIG. 5 shows glucose or cytochalasin B inhibited glucose-binding of insulin-F on erythrocyte ghosts.

In order to conjugate GLUT inhibitors to GLUT, the GLUT inhibitors were first functionalized with an amino group to facilitate their conjugation to insulin (FIGS. 2 and 3). For forskolin, the introduction of the amino group and alkyl chains can enhance its binding affinity to GLUT. For inhibitor 2 (In2), an amino group was introduced through Michael addition reaction while maintaining the main structures unchanged. In order to conjugate insulin to forskolin and inhibitor 2, insulin was firstly reacted with Traut's reagent to introduce a thiol group and used directly for conjugating inhibitors, which was also beforehand reacted with SMCC crosslinker. The obtained conjugates insulin-forskolin and insulin-In2 were insoluble at pH 7.4 and the structure was confirmed by MALDI-TOF mass spectrum. Using erythrocyte ghosts as the model of glucose transporter, insulin-F was found to be able to bind to membrane (FIG. 4). In addition, this binding could be inhibited by a reported glucose transporter inhibitor, cytochalasin B, and glucose (FIG. 5), indicating the binding is GLUT specific.

Figure 6:
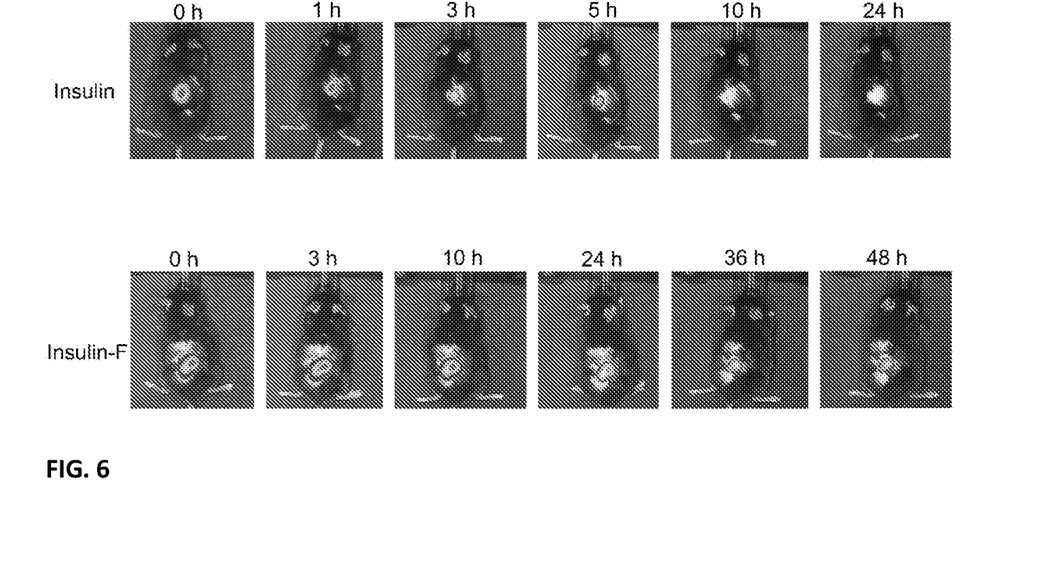
FIG. 6 shows living imaging of diabetic mice subcutaneously injected with insulin or insulin-F. Insulin or insulin-F was labeled with Cy5.
Figure 7:
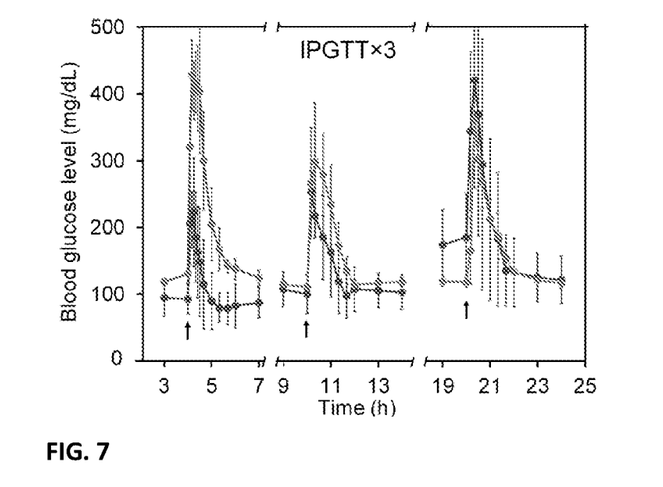
FIG. 7 shows multiple glucose tolerance test. Insulin-F was subcutaneously injected. The dose was set to 400 IU/kg for insulin conjugate. Error bars represent the S.D. of three independent experiments (n=5).

The in vivo therapeutic efficacy of insulin conjugates was evaluated in type 1 diabetic mouse model induced by STZ. The diabetic mice were assigned to four groups treated with insulin conjugates or native insulin. PBS was used as a control. The BGLs of all treated groups decreased to below 200 mg/dL within 0.5 h, indicating the retention of activity of insulin conjugates (FIG. 4). Moreover, blood glucose level of mice treated by insulin conjugates was maintained within the normal range (<200 mg/dL) for more than 10 hours, much longer than the three hours associated with free insulin. Also, negligible hypoglycemia was observed in mice treated with insulin conjugates. The binding of insulin conjugate to GLUT on living cells helped reduce the blood insulin level, making the hypoglycemia less likely to occur. The long-lasting behavior of insulin-F was further confirmed using living imaging (FIG. 6). Furthermore, a multiple intraperitoneal glucose tolerance test further confirmed the long-lasting blood-glucose-regulating ability of insulin-F (FIG. 7). This fast-regulation of blood glucose level from hyperglycemia to normoglycemia may due to the hyperglycemia-triggered insulin-F release from glucose transporter.

In summary, subcutaneously injectable glucose-responsive insulin conjugates with inhibitors of GLUT have been synthesized. In addition, it was insoluble in PBS at pH 7.4, and released basal insulin under a normal glucose level. Once subcutaneously injected, insulin conjugate forms depot under the skin, which constantly releases insulin to blood and systemic circulation. The GLUT on living cells can capture and bind to insulin conjugate under normoglycemia, buffering the initial high level of insulin and making the hypoglycemia negligible. In addition, this insulin pool can release insulin under a hyperglycemic state from cell membranes into circulation, therefore regulating blood glucose level in a real-time manner. The in vivo animal experiment demonstrated that this insulin conjugate can regulate BGL efficiently.

REFERENCES

A. D. Association, *Clinical Diabetes* 2017, 35, 5-26.

A. Matsumoto, R. Yoshida, K. Kataoka, *Biomacromolecules* 2004, 5, 1038-1045;

A. Sasaki, K. Nagatomo, K. Ono, T. Yamamoto, Y. Otsuka, T. Teshima, K. Yamada, *Human cell* 2016, 29, 37-45

A. Solini, C. Rossi, C. M. Mazzanti, A. Proietti, H. Koepsell, E. Ferrannini, *Diabetes, Obesity and Metabolism* 2017

C. Higuchi, T. Sanaka, T. Sato, M. Omata, M. Watanabe, S. Mine, N. Inuzuka, H. Nihei, *ADVANCES IN PERITONEAL DIALYSIS* 1997, 13, 253-256

C. R. Gordijo, K. Koulajian, A. J. Shuhendler, L. D. Bonifacio, H. Y. Huang, S. Chiang, G. A. Ozin, A. Giacca, X. Y. Wu, *Advanced Functional Materials* 2011, 21, 73-82;

D. H.-C. Chou, M. J. Webber, B. C. Tang, A. B. Lin, L. S. Thapa, D. Deng, J. V. Truong, A. B. Cortinas, R. Langer, D. G. Anderson, *Proceedings of the National Academy of Sciences* 2015, 112, 2401-2406;

D. Shiino, Y. Murata, A. Kubo, Y. J. Kim, K. Kataoka, Y. Koyama, A. Kikuchi, M. Yokoyama, Y. Sakurai, T. Okano, *Journal of controlled release* 1995, 37, 269-276;

J. D. Robbins, A. Laurenza, R. W. Kosley Jr, G. J. O'Malley, B. Spahl, K. B. Seamon, *Journal of medicinal chemistry* 1991, 34, 3204-3212.

J. R. Ehrenkranz, N. G Lewis, C. R. Kahn, J. Roth, *Diabetes Metab Res Rev* 2005, 21, 31-38

J. Yu, Y. Zhang, Y. Ye, R. DiSanto, W. Sun, D. Ranson, F. S. Ligler, J. B. Buse, Z. Gu, *Proc Natl Acad Sci USA* 2015, 112, 8260-8265.

K. Kapoor, J. S. Finer-Moore, B. P. Pedersen, L. Caboni, A. Waight, R. C. Hillig, P. Bringmann, I. Heisler, T. Muller, H. Siebeneicher, *Proceedings of the National Academy of Sciences* 2016, 113, 4711-4716.

K. M. Bratlie, R. L. York, M. A. Invernale, R. Langer, D. G Anderson, *Adv Healthc Mater* 2012, 1, 267-284;

K. Podual, F. J. Doyle, N. A. Peppas, *Journal of Controlled Release* 2000, 67, 9-17

L. Lu, A. Lundqvist, C.-M. Zeng, C. Lagerquist, P. Lundahl, *Journal of Chromatography A* 1997, 776, 81-86.

M. Brownlee, A. Cerami, *Diabetes* 1983, 32, 499-504; b) C. Wang, Y. Ye, W. Sun, J. Yu, J. Wang, D. S. Lawrence, J. B. Buse, Z. Gu, *Advanced Materials* 2017, 29.

M. F. Shanahan, S. A. Olson, M. J. Weber, G. E. Lienhard, J. C. Gorga, *Biochemical and biophysical research communications* 1982, 107, 38-43

M. L. Macheda, S. Rogers, J. D. Best, *Journal of cellular physiology* 2005, 202, 654-662.

N. Manel, F. J. Kim, S. Kinet, N. Taylor, M. Sitbon, J.-L. Battini, *Cell* 2003, 115, 449-459.

N. Peppas, Y. Huang, M. Torres-Lugo, J. Ward, J. Zhang, *Annual review of biomedical engineering* 2000, 2, 9-29.

N. Yan, *Journal of Molecular Biology* 2017, 429, 2710-2725.

O. Veiseh, B. C. Tang, K. A. Whitehead, D. G. Anderson, R. Langer, *Nat Rev Drug Discov* 2015, 14, 45-57.

R. L. Ingermann, J. M. Bissonnette, P. L. Koch, *Biochimica et Biophysica Acta (BBA)-Biomembranes* 1983, 730, 57-63

S. Kohler, A. Salsali, S. Hantel, S. Kaspers, H. J. Woerle, G. Kim, U. C. Broedl, *Clinical Therapeutics* 2016, 38, 1299-1313

V. R. Lavis, D. P. Lee, S. Shenolikar, *Journal of Biological Chemistry* 1987, 262, 14571-14575

W. L. Brooks, B. S. Sumerlin, *Chemical reviews* 2015, 116, 1375-1397.

X. Hu, J. Yu, C. Qian, Y. Lu, A. R. Kahkoska, Z. Xie, X. Jing, J. B. Buse, Z. Gu, *ACS Nano* 2017, 11, 613-620.

Y. Ito, M. Casolaro, K. Kono, Y. Imanishi, *Journal of controlled release* 1989, 10, 195-203

Y. Lu, A. A. Aimetti, R. Langer, Z. Gu, *Nature Reviews Materials* 2016, 2, 16075.

Y. Ohkubo, H. Kishikawa, E. Araki, T. Miyata, S. Isami, S. Motoyoshi, Y. Kojima, N. Furuyoshi, M. Shichiri, *Diabetes research and clinical practice* 1995, 28, 103-117.

Z. Gu, A. A. Aimetti, Q. Wang, T. T. Dang, Y. Zhang, O. Veiseh, H. Cheng, R. S. Langer, D. G Anderson, *ACS Nano* 2013, 7, 4194-4201.

Z. Gu, T. T. Dang, M. Ma, B. C. Tang, H. Cheng, S. Jiang, Y. Dong, Y. Zhang, D. G Anderson, *ACS Nano* 2013, 7, 6758-6766.

What is claimed is:

1. A glucose responsive insulin system comprising;
   a) a glucose transporter binding structure comprising an insulin moiety conjugated to at least one competitive inhibitor of glucose transporter; wherein the competitive inhibitor of the glucose transporter comprises Inhibitor 2 (In2), and
   b) wherein the glucose transporter binding structure is configured to reversibly bind a glucose transporter, and
   c) wherein the glucose transporter binding structure releases a portion of the insulin in high glucose conditions.

2. The composition of claim 1, wherein the competitive inhibitor has a greater affinity for the glucose transporter than D-glucose.

3. The composition of claim 1, wherein the glucose transporter comprises a GLUT protein.

4. The composition of claim 3, wherein the GLUT protein is a GLUT1 protein.

5. The composition of any one of claim 1, wherein high glucose conditions are greater than or equal to 200 mg/dL.

6. The composition of any one of claim 1, wherein the glucose transporter binding structure binds the glucose transporter in low glucose conditions, wherein low glucose conditions are from 0 up to 200 mg/dL.

7. The composition of claim any one of claim 1, wherein the glucose transporter binding structure is insoluble at pH 7.4.

8. A method of controlling glucose levels in a subject, the method comprising;
   a) administering a therapeutically effective amount of a composition to a subject having diabetes, the composition comprising;
   b) a glucose transporter binding structure comprising an insulin moiety conjugated to at least one competitive inhibitor of glucose transporter; wherein the competitive inhibitor of the glucose transporter comprises Inhibitor 2 (In2);
   c) wherein the glucose transporter binding structure is configured to reversibly bind a glucose transporter; and
   d) wherein the glucose-binding structure releases a portion of the glucose-modified insulin in high glucose conditions.

9. The method of claim 8, wherein the glucose transporter is expressed on a red blood cell.

10. The method of claim 9, wherein the red blood cell is human.

11. The method of any one of claim 8, wherein high glucose conditions are greater than or equal to 200 mg/dL.

12. The method of any one of claim 8, wherein the glucose transporter binding structure binds the glucose transporter in low glucose conditions, wherein low glucose conditions are from 0 up to 200 mg/dL.

13. The method of any one of claim 8, wherein the composition is administered to the subject using a transdermal patch.

14. The method of any one of claim 8, wherein the composition is administered to the subject using a microneedle-array patch.

15. The method of any one of claim 8, wherein the subject has type I diabetes.

16. The method of any one of claim 8, wherein the subject has type II diabetes.

* * * * *